(12) United States Patent
Kato et al.

(10) Patent No.: US 10,869,613 B2
(45) Date of Patent: Dec. 22, 2020

(54) MEDICAL GUIDANCE DEVICE

(71) Applicant: Canon USA Inc., Melville, NY (US)

(72) Inventors: Takahisa Kato, Brookline, MA (US); Elizabeth Rogers Kelly, Arlington, MA (US)

(73) Assignee: Canon U.S.A., Inc., Melville, NY (US)

( * ) Notice: Subject to any disclaimer, the term of this patent is extended or adjusted under 35 U.S.C. 154(b) by 403 days.

(21) Appl. No.: 15/379,300

(22) Filed: Dec. 14, 2016

(65) Prior Publication Data

US 2017/0172458 A1 Jun. 22, 2017

Related U.S. Application Data

(60) Provisional application No. 62/268,378, filed on Dec. 16, 2015.

(51) Int. Cl.
| | | |
|---|---|---|
| *A61B 5/06* | (2006.01) | |
| *A61B 5/11* | (2006.01) | |
| *A61B 17/34* | (2006.01) | |
| *A61B 5/00* | (2006.01) | |
| *A61B 90/00* | (2016.01) | |
| *A61B 34/20* | (2016.01) | |
| *A61B 17/00* | (2006.01) | |

(52) U.S. Cl.
CPC ............ *A61B 5/067* (2013.01); *A61B 5/062* (2013.01); *A61B 5/1127* (2013.01); *A61B 5/1128* (2013.01); *A61B 5/742* (2013.01); *A61B 17/3403* (2013.01); *A61B 5/6848* (2013.01); *A61B 2017/00438* (2013.01); *A61B 2017/00442* (2013.01); *A61B 2017/3413* (2013.01); *A61B 2034/2048* (2016.02); *A61B 2090/3983* (2016.02); *A61B 2562/0219* (2013.01)

(58) Field of Classification Search
CPC ........... A61B 34/10; A61B 34/20; A61B 5/11; A61B 6/032; A61B 5/067; A61B 5/062; A61B 5/1127; A61B 5/1128; A61B 5/742; A61B 17/3403; A61B 2034/2048; A61B 2090/3983; A61B 5/6848; A61B 2017/00438; A61B 2017/00442; A61B 2017/3413; A61B 2562/0219
See application file for complete search history.

(56) References Cited

U.S. PATENT DOCUMENTS

| | | | | |
|---|---|---|---|---|
| 6,122,538 A | * | 9/2000 | Sliwa, Jr. ................. | A61B 8/00 324/207.14 |
| 6,132,379 A | * | 10/2000 | Patacsil ..................... | A61B 8/06 600/459 |
| RE39,133 E | * | 6/2006 | Clayton ............. | A61B 17/7083 600/426 |
| 7,867,199 B2 | * | 1/2011 | Mogensen ............ | A61M 5/158 604/164.04 |
| 8,241,301 B2 | | 8/2012 | Zhang et al. | |

(Continued)

*Primary Examiner* — Malina D. Blaise
(74) *Attorney, Agent, or Firm* — Canon U.S.A., Inc., IP Division (57) ABSTRACT

This application provides a medical guidance device with an inertial measurement unit and a mechanical interface. This device can provide accurate and precise orientation of insertable medical tools is critical in surgical procedure, such as for placement of a needle-like instrument according to plan based on medical images (e.g., computed tomography (CT) and Magnetic Resonance Imaging (MRI)) in percutaneous interventions.

22 Claims, 7 Drawing Sheets

(56) References Cited

U.S. PATENT DOCUMENTS

| | | | | |
|---|---|---|---|---|
| 8,957,812 | B1* | 2/2015 | Hill | G01S 5/0027 342/445 |
| 10,123,767 | B2* | 11/2018 | Andrews | A61B 8/483 |
| 10,602,958 | B2* | 3/2020 | Silverstein | A61B 5/743 |
| 2003/0208122 | A1 | 11/2003 | Melkent et al. | |
| 2004/0260312 | A1* | 12/2004 | Magnusson | A61B 17/3403 606/130 |
| 2006/0229641 | A1* | 10/2006 | Gupta | A61B 17/3403 606/130 |
| 2007/0149880 | A1* | 6/2007 | Willis | A61B 8/0841 600/471 |
| 2008/0208041 | A1* | 8/2008 | Gilboa | A61B 6/12 600/426 |
| 2008/0221519 | A1* | 9/2008 | Schwach | A61B 8/4209 604/116 |
| 2009/0112084 | A1* | 4/2009 | Piferi | A61B 5/055 600/421 |
| 2010/0082040 | A1* | 4/2010 | Sahni | A61B 17/3403 606/130 |
| 2010/0094116 | A1* | 4/2010 | Silverstein | A61B 5/06 600/409 |
| 2011/0098569 | A1* | 4/2011 | Warmath | G09B 23/285 600/443 |
| 2011/0137156 | A1* | 6/2011 | Razzaque | A61B 18/1477 600/424 |
| 2011/0190787 | A1* | 8/2011 | Sahni | A61B 90/11 606/130 |
| 2012/0143029 | A1* | 6/2012 | Silverstein | A61B 5/7475 600/374 |
| 2012/0319859 | A1 | 12/2012 | Taub et al. | |
| 2013/0066334 | A1* | 3/2013 | Schoepp | A61B 90/11 606/130 |
| 2014/0100421 | A1* | 4/2014 | Dejima | A61B 1/00052 600/101 |
| 2014/0148808 | A1* | 5/2014 | Inkpen | G01B 7/003 606/80 |
| 2014/0236019 | A1* | 8/2014 | Rahum | A61B 5/0075 600/473 |
| 2014/0276001 | A1* | 9/2014 | Ungi | A61B 90/39 600/424 |
| 2014/0276559 | A1* | 9/2014 | Page | A61B 17/3403 604/506 |
| 2015/0142372 | A1* | 5/2015 | Singh | A61B 5/4851 702/150 |
| 2015/0157384 | A1* | 6/2015 | Hoey | A61B 18/04 600/104 |
| 2015/0190090 | A1* | 7/2015 | Silverman | A61B 5/02007 600/363 |
| 2015/0209113 | A1 | 7/2015 | Burkholz et al. | |
| 2016/0022146 | A1* | 1/2016 | Piron | A61B 90/39 600/411 |
| 2016/0157887 | A1* | 6/2016 | Kim | A61B 17/3403 600/424 |
| 2016/0258744 | A1* | 9/2016 | Shimaoka | G01B 11/14 |
| 2016/0278746 | A1 | 9/2016 | Hancu et al. | |
| 2017/0014200 | A1* | 1/2017 | Onuma | A61B 17/3403 |
| 2017/0348061 | A1* | 12/2017 | Joshi | A61M 5/172 |
| 2018/0168682 | A1* | 6/2018 | Hazard, III | A61B 8/12 |
| 2019/0282262 | A1* | 9/2019 | Bouazza-Marouf | A61B 17/3403 |

* cited by examiner

MEDICAL GUIDANCE DEVICE

CROSS-REFERENCE TO RELATED APPLICATION(S)

This application claims priority to U.S. Provisional Application Ser. No. 62/268,378 filed 16 Dec. 2015, the content of which is incorporated herein by reference in its entirety.

FIELD OF THE DISCLOSURE

The disclosure of this application generally relates to medical devices and in particular to a medical guidance device with an inertial measurement unit and a mechanical interface.

BACKGROUND INFORMATION

Accurate and precise orientation of insertable medical tools is critical in surgical procedure, especially for placement of a needle-like instrument according to plan based on medical images, such as computed tomography (CT) and Magnetic Resonance Imaging (MRI) in percutaneous interventions.

Also intuitive understanding of the orientation of the insertable medical tools palliates difficulty of the surgical procedures. To achieve an accurate and intuitive orientation of the insertable medical tools, and to reduce its user dependency, a variety of systems have been used.

For example, puncturing needle guiding devices are either placed on the patient or positioned above the patient and hold the needle. An angle guidance means allows the physician or other practitioner to manually adjust the needle angle within the device and guide the needle to aim a target lesion with this device. See, for example, U.S. Pat. No. 8,241,301. However, devices such as this have significant limitations, including that they do not directly provide real-time orientation of the needle to be inserted into a patient body. Therefore, practitioners still have risk with this device to include orientation errors caused by dislocation of the device from the aligned position and orientation, and a mechanical gap between the guidance means and the needle. Also, the device needs to be held at aligned position and orientation through the procedure. With holding either with practitioner's hand or with a mounting device, the workflow needs to include additional steps and devices from the standard manual procedure except for the guidance device itself.

U.S. Pat. Pub. 2015/0157384 discloses a vapor delivery system and method to insert a vapor delivery needle to deliver condensable vapor energy to treating prostate tissue. To localize the needle automatically, the vapor delivery system includes inertial navigation chips that include accelerometers and gyroscopes. However, this system still has limitations. For example, it cannot guide versatile insertable medical tools with the same sensing system. Also, the sensing system is associated with the device body firmly without any other reference sensors. Therefore, it is difficult to select any reference that practitioner want to use to guide the needle.

Thus, there is need for a medical guidance device that overcomes these and other limitations and provides accurate and precise orientation of insertable medical tools.

SUMMARY OF EXEMPLARY EMBODIMENTS

According to at least one embodiment of the invention, there is provided a medical guidance device comprising: an angular sensor and a mechanical interface attached to the angular sensor. The mechanical interface is configured to be removably attached to an insertable medical tool or a physician or other practitioner's hand and the angular sensor (which comprises an inertial measurement unit comprising at least one sensor that is a gyroscope, an accelerometer or a magnetometer, and a circuit board connected to the inertial measurement unit and configured to compute an orientation by processing sensed signals from the inertial measurement unit) is configured to determine an orientation of the insertable medical tool or the practitioner's hand. The medical guidance device may also include an indicator that receives information about the orientation from the angular sensor and indicates the orientation of the insertable medical tool or practitioner's hand.

According to other embodiments of the invention, there is provided a medical guidance system comprising a plurality of medical guidance devices and a processor electrically connected to the plurality of medical guidance devices. The processor sets one of the plurality of medical guidance devices as a reference device, and measures discrepancies between an orientation of the reference device and orientations of the other medical guidance devices.

According to yet other embodiments of the invention, there is provided a medical guidance system comprising: at least one medical guidance device attached on a needle-like device; fiducial markers on a patient that are aligned to a skin entry point where the needle-like device is inserted, and a console electrically connected to an image server and the medical guidance device. In use, the console receives a medical image, and registers a position and an orientation of the fiducial markers to a coordinate system of the patient, and feedback the orientation from the medical guidance device on the medical image by using the skin entry point as a reference position.

In other embodiments there is provided a method of deploying an insertable medical tool into a patient comprising: attaching a mechanical interface to an insertable medical tool, wherein the mechanical interface is part of a medical guidance device that comprises: an angular sensor comprising an inertial measurement unit comprising at least one sensor that is a gyroscope, an accelerometer or a magnetometer, and a circuit board connected to the inertial measurement unit, a mechanical interface attached to the angular sensor, and an indicator. The method further comprises defining a reference orientation, aligning insertable medical tool with reference orientation based on feedback from the indicator, and deploying the insertable medical tool into the patient.

In yet other embodiments, there is provided a method of aiding in the deployment of an insertable medical tool comprising: providing the insertable medical tool as described herein above, accepting reference orientation information via a user input; evaluating discrepancy between insertable medical tool orientation and/or location compared to the reference orientation; and providing discrepancy information via the indicator. This discrepancy information (feedback) may be in real time.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 1(A) is a side view of the medical guidance device. FIG. 1(B) is a cross sectional view at B-B line in FIG. 1(A). FIG. 1(C) is a side view of the medical guidance device when the device is attached on an insertable medical tool 7.

FIGS. 7(A)-7(C) show exemplary mechanical interface for the second embodiment.

FIG. 8(A) is a perspective view and FIG. 8(B) is cross sectional view at K-K line in FIG. 8(A)).

FIG. 9(A) is a perspective view and FIG. 9(B) is another perspective view including an insertable medical tool.

FIG. 10(A) is a top view that includes a user's hand. FIG. 10(B) is a side view.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

Embodiment 1

Figure 1:
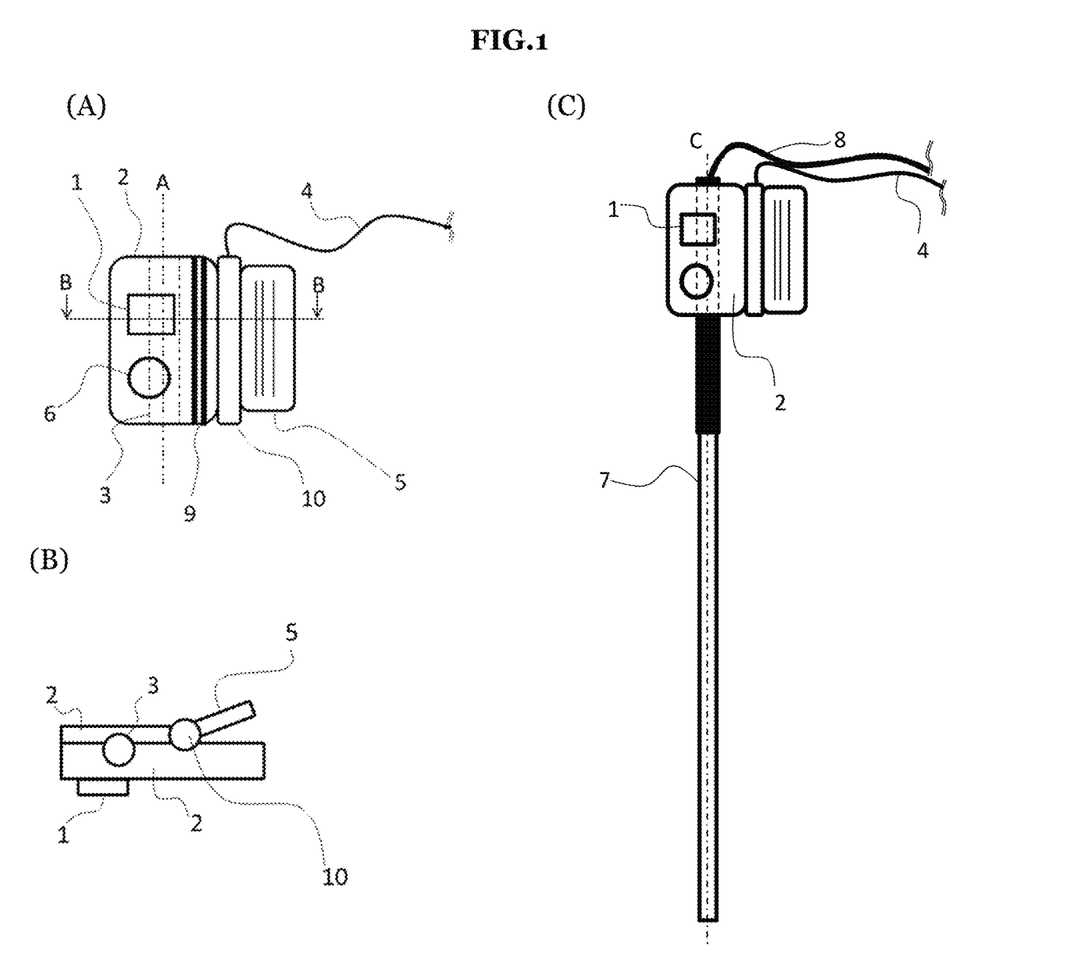
FIG. 1 is an exemplary medical guidance device.

A first embodiment will now be described with reference to FIGS. 1 to 6 and FIG. 8, where FIG. 1 illustrates an exemplary medical guidance device. The medical guidance device in this embodiment comprises angular sensor 1, mechanical interface 2, tool guide 3, cable 4, handle 5, button 6, reference marker 9 and hinge 10. Angular sensor 1 includes an inertial measurement unit with a 3-axis gyroscope, a 3-axis accelerometer and a 3-axis magnetometer and circuit boards. The circuit boards are electrically connected the inertial measurement unit and computes an absolute orientation of angular sensor 1 based on a coordinate system of angular sensor 1 that is programmable with circuit boards. Specifically, the circuit boards use all measurements from the 3-axis gyroscope, the 3-axis accelerometer and the 3-axis magnetometer to achieve balance between stable sensing without drifting and measurement update fast enough to regard the speed as real-time for the medical procedure. Specifically, in this embodiment, the measurement update speed ranges from 20 Hz to 100 Hz.

The inertial measurement unit within the angular sensor 1 has with one or more of gyroscopes, accelerometers and magnetometers and, in some preferable embodiments, each of gyroscopes, accelerometers and magnetometers can provide combination of high frequency and accurate sensing of the orientation. The gyroscope, accelerometer and magnetometer may be incorporated onto a single chip with an integrated output, or they may be separate. The inertial measurement unit also allows for reducing the drifting of the sensed orientation through long duration of usage for the operation. Therefore, the physician or other practitioner can guide the medical device with the accurate orientation at real-time for manual operation through the operation.

The mechanical interface 2 can be attached and detached to insertable medical tool 7 with tool guide 3 (FIG. 1 (C)). Axis A is a center line of tool guide 3, and is aligned with axis C that is a centroid of insertable medical tool 7 in the attachment mode. Moreover, angular sensor 1 is fixed on mechanical interface 2 with designed (known) geometrical relation to tool guide 3 and can register its rotation relation to insertable medical tool 7 to the coordinate system of angular sensor 1 by using this designed geometrical relation. The angular sensor 1 may be directly attached to the mechanical interface 2 or may be indirectly attached with a known geometrical relation.

The insertable medical tool 7 is depicted in this embodiment as a long, needle-like apparatus. However, medial tools having other form factors may also be used in the present invention.

The mechanical interface 2 of the exemplary medical guidance device includes handle 5, hinge 10 for this attaching features.

Figure 8:
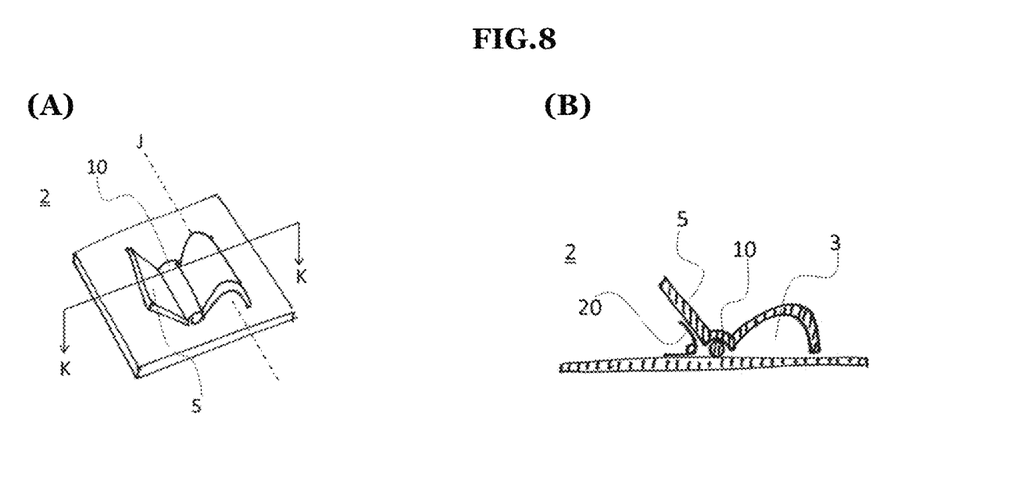
FIG. 8 shows an exemplary attachment mechanism for the medical guidance device.

FIG. 8 depicts detail principal for this attachment function. Mechanical interface 2 in this embodiment holds insertable medical tool 7 with spring 20 in hinge 10 (FIG. 8 (B) as cross sectional view at K-K line in FIG. 8 (A)). The practitioner can, for example, press handle 5 to open tool guide 3 and attaches tool guide 3 to insertable medical tool 7 along axis J with optional alignment between center line K of tool guide 3 and centroid of insertable medical tool 7.

Figure 2:
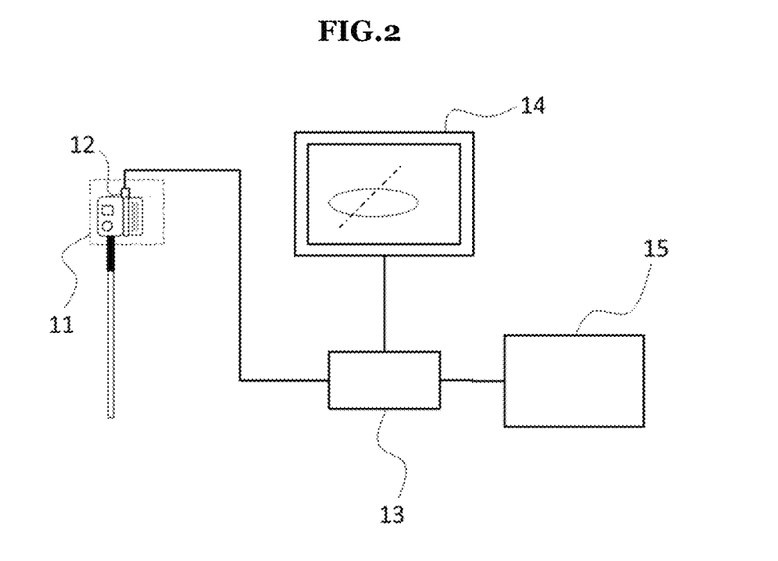
FIG. 2 shows a block diagram of the embodiment of FIGS. 1(A)-(C).

FIG. 2 shows a block diagram of this embodiment. Medical guidance device 11 is electrically connected to console 13 via signal interface 12. This connection also supplies a power for angular sensor 1. Console 13 is further connected to indicator 14 and image server 15. Console 13 receives medical images, for example CT or MRI images, from image server 15 that is, for example, a DISCOM server connected to medical imaging devices. The medical images are also sent to indicator 14 with annotated information to help the physician or other practitioner to plan the medical procedure by console 13.

Also, console 13 can be adopted to interact with the practitioner to define a reference orientation with the medical images. The reference orientation is sent to medical guidance device 11 via signal interface 12. For example, during planning, a practitioner can define the reference orientation after viewing one or more medial image(s). Several reference orientations can be defined for procedures that require more than one deployment (e.g., multiple needle placements). This information can be sent to the medical guidance device and the device will then aid the practitioner with one or more types of feedback when the practitioner moves the insertable medical tool attached to the medical guidance device.

Medical guidance device 11 can also determine discrepancy between the reference orientation and the orientation of the insertable medical tool 7 by using registered rotation of the medical images based on the coordinate of medical guidance device 11. The signal interface can enable the circuit board(s) to compare the real-time orientation of the insertable medical tools with the target orientation and to evaluate discrepancy between them. The circuit board may be a combination of a controller or other features commonly found in a computer as discussed below. Therefore, the practitioner can perform the procedure reducing discrepancy between the plan and the execution. This discrepancy can be, for example, displayed on the indicator 14 as an image or a signal, such as a beep, vibration, or light indicates the relative amount of the discrepancy. This feedback can be provided in real time.

The circuit board may be connected to a data storage unit. This data storage unit stores the reference orientation and/or the orientation of the insertable medical tool. The orientation stored by the data storage unit can be used, for example, to evaluate similarity or discrepancy among the orientations at different time. With the similarity or the discrepancy, practitioner can analyze previous or present operations and also can plan the operation to improve or reproduce the operation. By storing the reference orientation that practitioner is interested in, the medical guidance device can evaluate discrepancy between the reference orientation and the real-time orientation. With this discrepancy, the practitioner can orient the medical device at the certain relation from the reference orientation that practitioner is interested in or can reproduce the same orientation as the reference orientation quickly and accurately. The reference orientation can be an angle of the last insertion in the same insertable medical tool, or an angle of the insertion of the former insertable medical tool when the physician or other practitioner inserts multiple insertable medical tools for the patient.

Also, since practitioner can update the reference orientation quickly, the system can reduce the orientation error of the angular sensor 1, especially drifting error for long duration. The practitioner can the real-time orientation information within certain short duration after updating the reference orientation.

Figure 3:
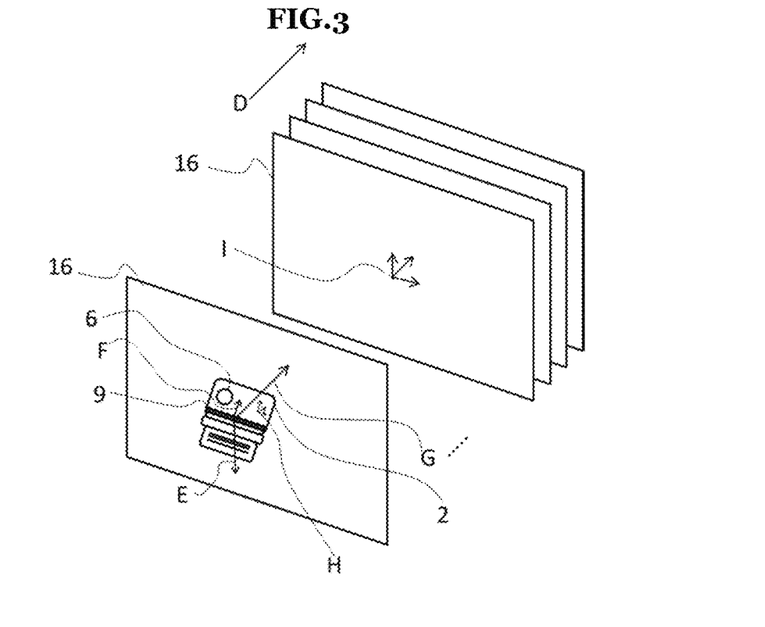
FIG. 3 is an illustration one of registration methods for rotation between the medical images and medical guidance device.

FIG. 3 illustrates one of registration methods for rotation between the medical images and medical guidance device 11. In this exemplary registration, before actual usage of medical guidance device 11 for the medical procedure, the practitioner holds and orient medical guidance device 11 to image plane direction D. Reference marker 9 on mechanical interface 2 is a hair line and is aligned to the direction of image plane 16. In this embodiment, the medical imaging device such as CT or MRI, provides image plane position with a line by projecting a laser line from a top of the medical imaging device. Reference marker 9 is aligned to the line manually. The practitioner can teach medical guidance device 11 about completion of the alignment by, for example, holding down button 9 for around 1 second.

Then, medical guidance device 11 measures gravitational direction E by using the accelerometers. Also, medical guidance device 11 already knows direction F that is normal direction from the hair line of reference marker 9. Therefore, with assumption that one of three axis in coordinate system I of medical image plane 16, i.e. the medical image plane 16 includes gravitational direction E, the medical guidance device 11 can determine medical image orientation G based on the coordinate H of medical guidance device 11. Therefore, medical guidance device 11 can register rotation of medical image plane 16 to its coordinate system.

Figure 4:
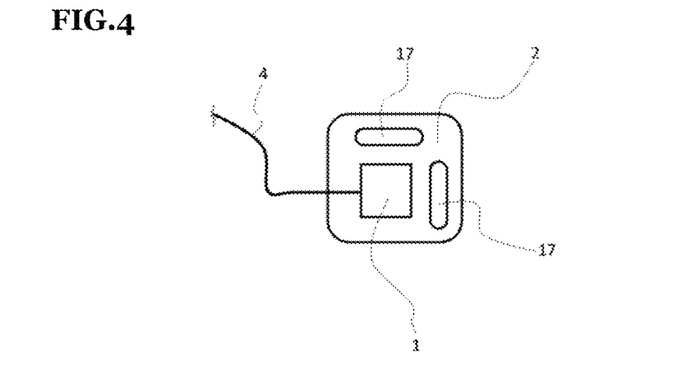
FIG. 4 illustrates another method for registration of a rotation between the medical images and medical guidance device.

FIG. 4 is another medical guidance device 11 mounted on patient for this rotation registration. Mechanical interface 2 of this embodiment may be, for example, an adhesive that can adhere to a skin on the patient. Also, mechanical interface 2 includes two fiducial markers that are visible in the medical imaging modality that the practitioner uses for the medical procedure.

First, two medical guidance devices 11, which are going to be attached to the patient and the insertable medical tool 7, are registered each other to the same coordinate system. This registration can be performed by using a mechanical flexure. The mechanical flexure aligns two medical guidance devices 11 to the same direction accurately. With this position, two medical guidance devices 11 can measure the orientations and sends the orientations to a processor in console 13. The processor in console 13 calibrates error between two orientations.

Second, the practitioner mounts medical guidance device 11 containing fiducial markers 17 on the patient skin and takes the medical images of the patient with fiducial markers 17. The medical images are sent to console 13. Then, console 13 performs image registration between the rotation of the medical image of the patient and medical guidance device 11 by using the image of fiducial markers 17.

Since the rotations between the medical guidance devices 11 on the patient and on insertable medical tool 7 are calibrated, the medical guidance device 11 on insertable medical tool 7 also are registered to the rotation of the medical image plane 16.

While this example provides two fiducial markers 17, the invention is not so limited. There may be any number, orientation, or type of fiducial or other markers used to calibrate and/or register the medical device 11 and/or insertable medical tool 7.

Figure 5:
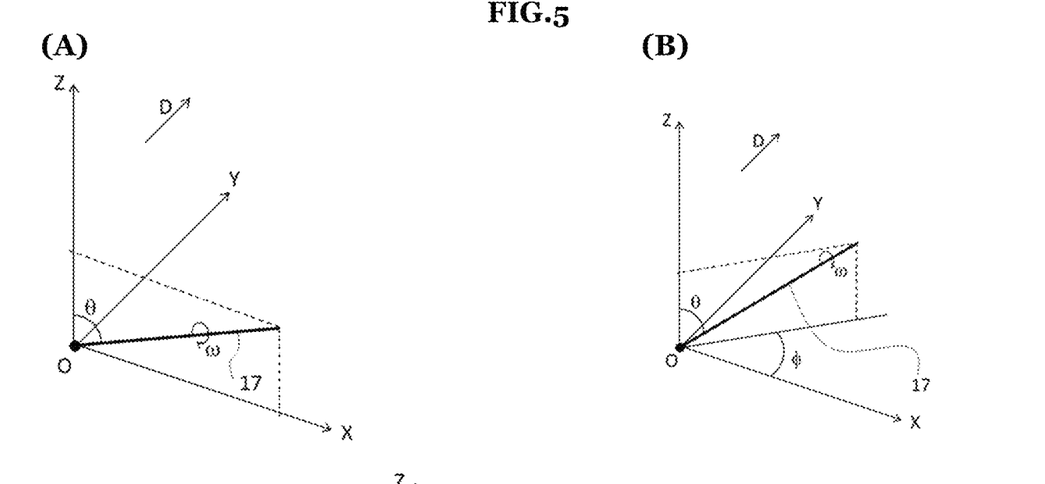
FIGS. 5(A) and 5(B) are representations that show how to map orientation in 3D space into two specific angles to use for the medical procedure.

FIG. 5 shows the coordinate of the medical image and it is explained how to map orientation in 3D space into two specific angles to use for a medical procedure involving insertion of the insertable medical tool 7 into a patient at the point O. Y axis is directing to the image scan direction D, and X and Z axis are on the medical image plane 16. Origin O locates at a skin entry point for the insertable medical tool 7, which is a needle-like tool for insertion into inside of the patient body.

In FIG. 5(A), tool orientation 17 is oblique to the medical image plane of X-Z plane and indicates an initial position the doctor places the insertable medical tool prior to insertion. The medical guidance device 11 maps tool orientation 17 in 3D space into insertion plane direction θ, insertion angle θ, and tool rotation co. Insertion plane direction θ inform relation between the image plane and the plane with insertion. When the practitioner need to insert the needle-like tool on the image plane, the practitioner can move the tool and confirm whether tool orientation 17 is on the image plane with φ=0 (FIG. 5 (B)). Also, insertion angle θ determined insertion orientation with insertion plane direction θ. Moreover, the medical guidance device 11 can provide tool rotation co to confirm orientation of the features on the insertable medical tool 7, for example a bevel tip in the needle-like device and camera in endoscopic device.

Figure 6:
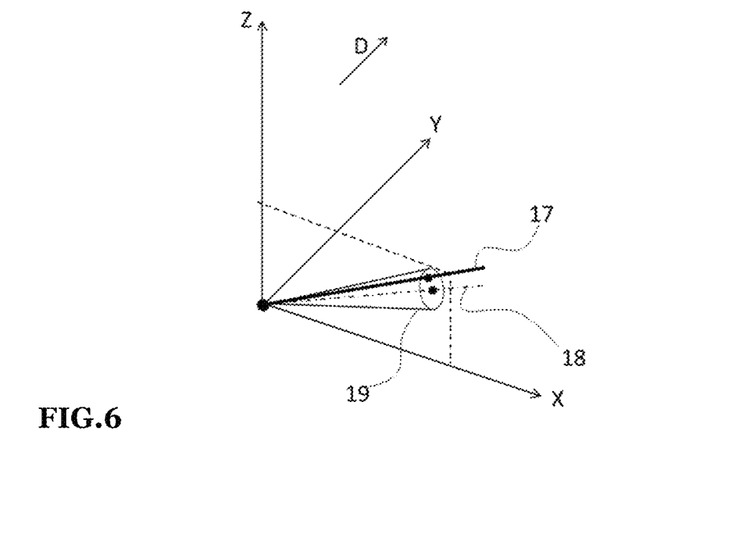
FIG. 6 shows the same coordinate system as in FIGS. 5(A) and 5(B), but also shows reference orientation 18.

In FIG. 6, the medical guidance device 11 can compute discrepancy between tool orientation 17 and reference orientation 18. This discrepancy can be an error norm of angle between tool orientation 17 and reference orientation 18. It also can be relative orientation with quaternion notation between them.

In some embodiments, the cable 4 is replaced by a wireless connection.

Medical guidance device 11 can also include tolerance orientation 19. Tolerance orientation 19 defines required accuracy of insertion. With tolerance orientation 19, the medical guidance device can give feedback whether tool orientation 17 is within tolerance by using indicator 14.

Embodiment 2

A second embodiment will now be described with reference to FIGS. 7, 9 and 10. Components similar to those of the first embodiment are denoted by the same reference numerals, and descriptions thereof are thus omitted. This embodiment is particularly different from the first embodiment is in the mechanical interface 2.

Figure 7:
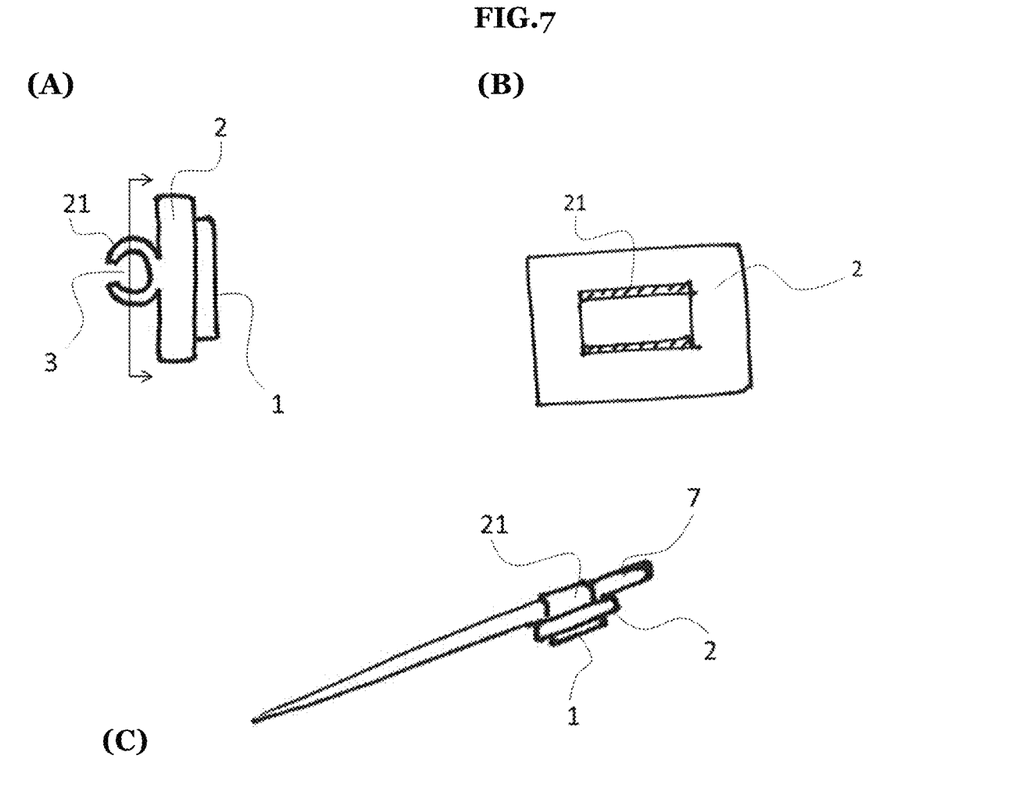
FIG. 7(A) is a top view showing a snap clip.
FIG. 7(B) is a side view and FIG. 7(C) shows the mechanical interface attached to an insertable medical tool.

FIG. 7 shows mechanical interface 2 in this embodiment. Mechanical interface 2 has snap clip 21 with tool guide 3. The snap clip 21 enables a reduced footprint of the mechanical interface 2 without additional hinge and handle. This is particularly advantageous in that can allow for a lighter guidance device. Since some embodiments require that the medical guidance device be situation on a needle, a lightweight device is important since it will not make the insertable medical tool 7 difficult to hold and move due to weight or uneven weight distribution.

Figure 9:
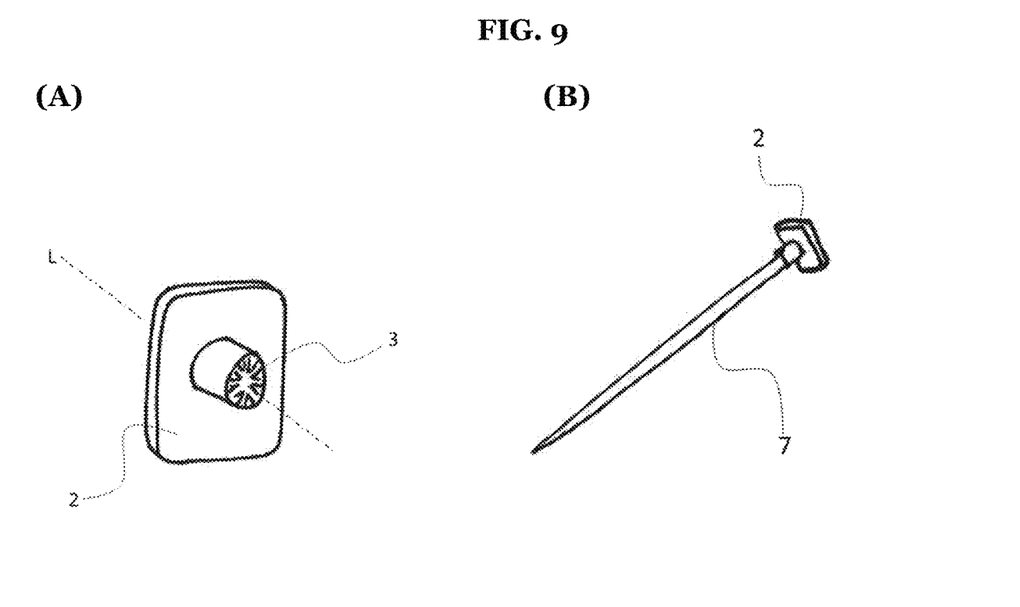
FIG. 9 shows another mechanical interface for the second embodiment.
Figure 10:
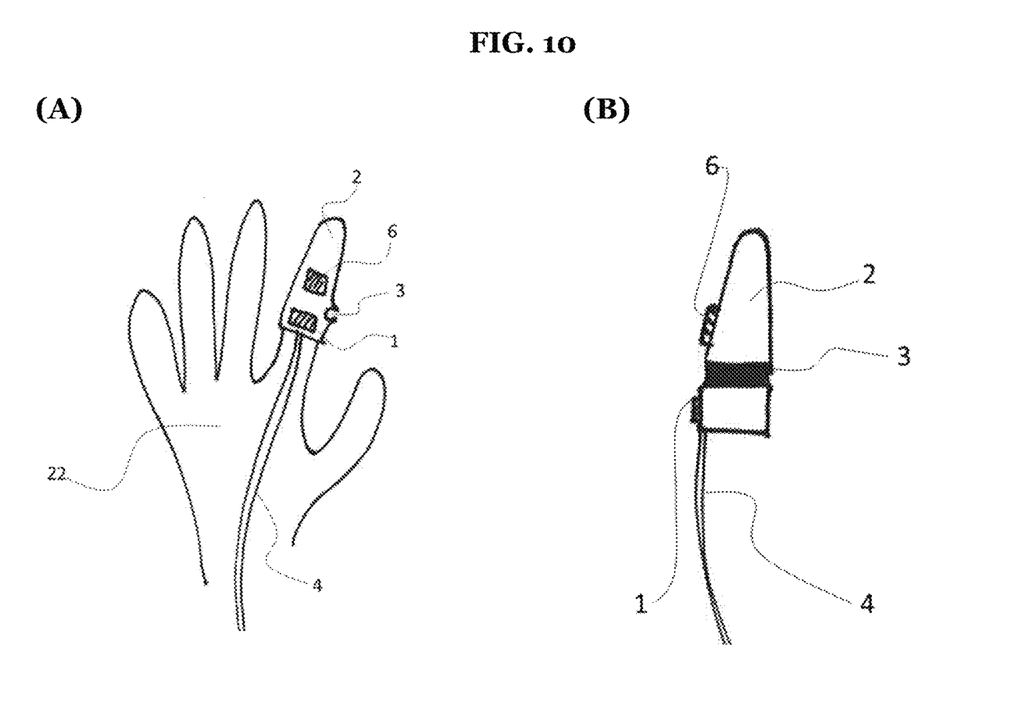
FIG. 10 shows yet another mechanical interface for the second embodiment.

Alternatively, another exemplary mechanical interface 2 is shown in FIG. 9. The mechanical interface 2 has cap feature with tool guide 3. This configuration maximizes a length of insertable medical tool 7 for holding and insertion by mounting it on the distal end of insertable medical tool 7. In some embodiments, an additional connector element is located be FIG. 10 shows yet another mechanical interface 2 in this embodiment.

Mechanical interface 2 has a finger cap for physician or other practitioner's hand 22.

Embodiment 3

A third embodiment will now be described with reference to FIGS. 11 and 12. Components similar to those of the first embodiment are denoted by the same reference numerals, and descriptions thereof are thus omitted. The main feature different from the first embodiment is indicator 14.

Figure 11:
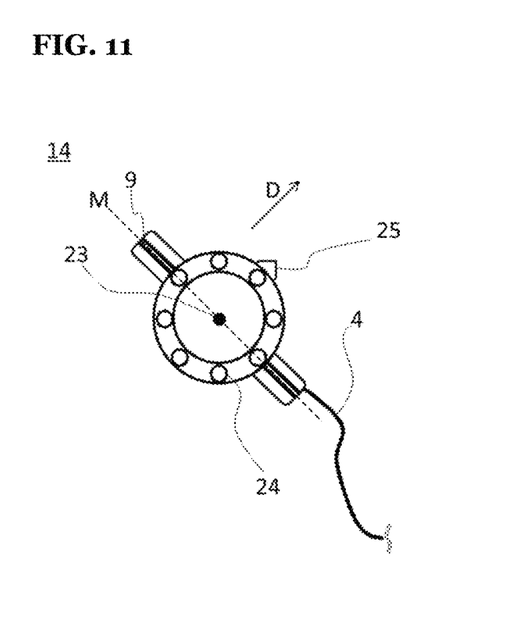
FIG. 11 shows the top view of an exemplary indicator.
Figure 12:
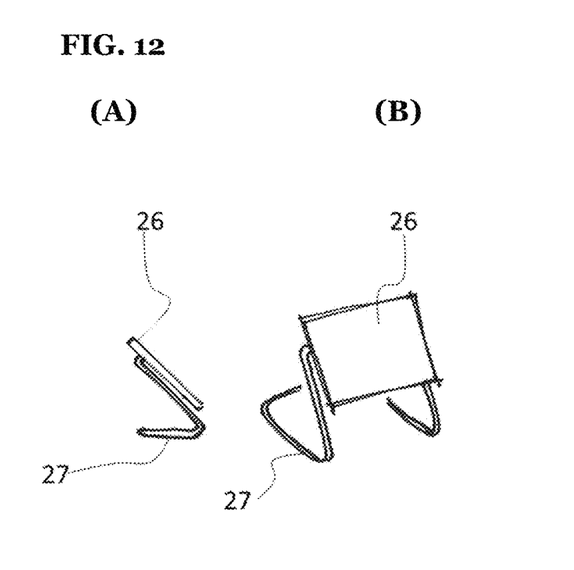
FIG. 12(A) is a side view and FIG. 12(B) is a perspective view of another exemplary indicator.

Indicator 14 in the embodiment of FIG. 11 may be mounted on the patient surrounding skin entry point 23. The indicator includes multi-color LEDs 24 along circular shape. Indicator 14 can optionally be aligned with image scan direction D by using reference marker 9 and arrow head marker 25. Multi-color LEDs 24 gives feedback of insertion plane direction of tool orientation 17 in real-time at relatively course interval of LED position, and shows error norm between tool orientation 17 and reference orientation 18 by changing colors of LEDs.

Indicator 14 also can show the insertion plane direction of the reference orientation by position of lighted LED with different color.

FIGS. 12(A) and 12(B) show another indicator 14 in this embodiment. Indicator 14 has touch screen display 26 and stand 27, and can be mounted on the bed or on the patient. Touch screen display show tool orientation 17 and reference orientation 18, and also can interact as a user interface to medical guidance device 11 with the practitioners.

Figure 13:
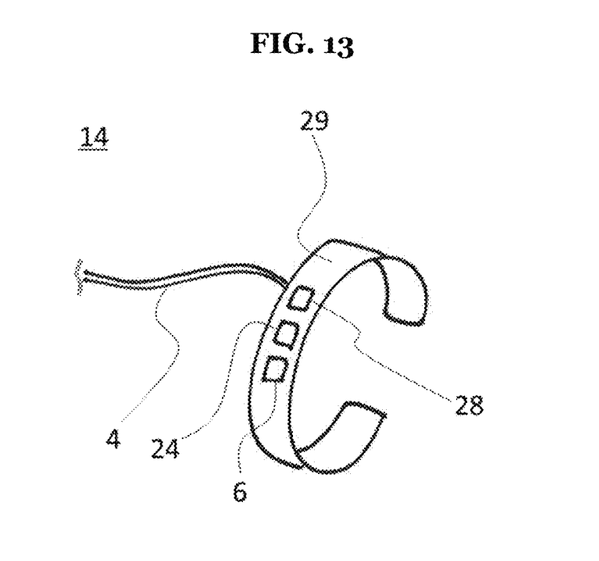
FIG. 13 is a perspective view of yet another exemplary indicator.

FIG. 13 is yet another indicator 14 in this embodiment. Indicator 14 includes a bracelet 29 as a second mechanical interface to be mounted on a practitioner's wrist. Indicator 14 can show error norm between reference orientation and tool orientation by changing color in multi-color LED 24 and also by vibration—changing vibration amplitude or pattern of a vibrator 29. Interface 14 also includes button 6, which may be a plurality of buttons or other input means to accept interaction from the practitioner.

In yet other embodiments, an indicator 14 may be located, for example, on the top of the mechanical interface 2 such as the mechanical interface shown in FIG. 9. In yet other embodiments, two or more indicators are provided. For example, a circular LED indicator similar to the indicator of FIG. 11 may be provided along with an indicator attached to the mechanical interface and providing vibration that is felt when holding the medical guidance device 2, insertable medical tool 7, or mechanical interface 2.

The indicator can give real-time feedback of the information of the orientation to the practitioner. The practitioner can have feedback almost instantaneously or at least within a second of, for example, moving the insertable medical tool and then can interpret the present orientation intuitively and interactively and can guide the insertable medical tools accurately. As discussed above, the feedback can be visual (either an image, or, for example, lights with changing intensities or colors), auditory, or even via small vibrations, dependent on the application and other types and modes of information the practitioner is accessing during the procedure.

By having the indicator and the medical guidance tool in the system, the system doesn't need additional system components, for instance an electromagnetic field generator in the system with an electromagnetic tracking device or observation camera and optical markers in the system with an optical tracking device, to guide the insertable medical tool. Therefore, the system can reduce the space to be used and the steps to be set up. Also, the system can reduce the human factor error from assembly and setup of the system. Moreover, the system can reduce time to setup for the system.

By mounting the indicator on the patient, the practitioner can look at the indicator near to an area for the medical procedure without large motion of eyes between the indicator and the insertable medical tools. In some embodiments, the indicator may surround or partially surround the skin entry point for the needle-like device can indicate the orientation along the trajectory around the skin entry point as a pivot. The indication can be easily confirmed by the practitioner with consistency to the real-time orientation relative to the reference orientation of the needle-like device. The practitioner doesn't need to change line of sight between the indicator and the needle-like device during the guidance.

By mounting the indicator on the bed or similarly near the patient, the indicator can be away from sterile field on the patient but be close enough for the practitioner to confirm the indication. Therefore, the indicator can be placed so as not to risk breaking the sterile field around the site. Also, the indicator can be mounted stably with a stable surface of the bed.

In other embodiments, the indicator is mounted on the physician or other practitioner. By mounting the indicator on the practitioners, the indicator doesn't need to occupy space on the patient and on the bed. Also, the indicator can locate close to the practitioner anytime. Moreover, the indicator can avoid cable tangling since the indicator is remote from the other insertable medical tools that mainly locate near to site for interest in medication. This also allows for tactile instead of visual feedback to the practitioner.

In some embodiments, there are two or more indicators. There may be a second or further mechanical interface that enables the associated indicator(s) to be mounted on variety of locations and angles. Therefore, the practitioners can get an optimal view of the indicator(s) on their needs by attaching the indicator at, for example, one of a variety of angels or positions along the insertable medical tool or patient that best suits their needs. Also, the practitioners can use multiple indicators among different practitioners and can share the real-time orientation among them.

Embodiment 4

A fourth embodiment will now be described with reference to FIGS. 14 and 15. Components similar to those of the first embodiment are denoted by the same reference numerals, and descriptions thereof are thus omitted. The main feature different from the first embodiment is mechanical interface 2 and tool guide 3.

Figure 14:
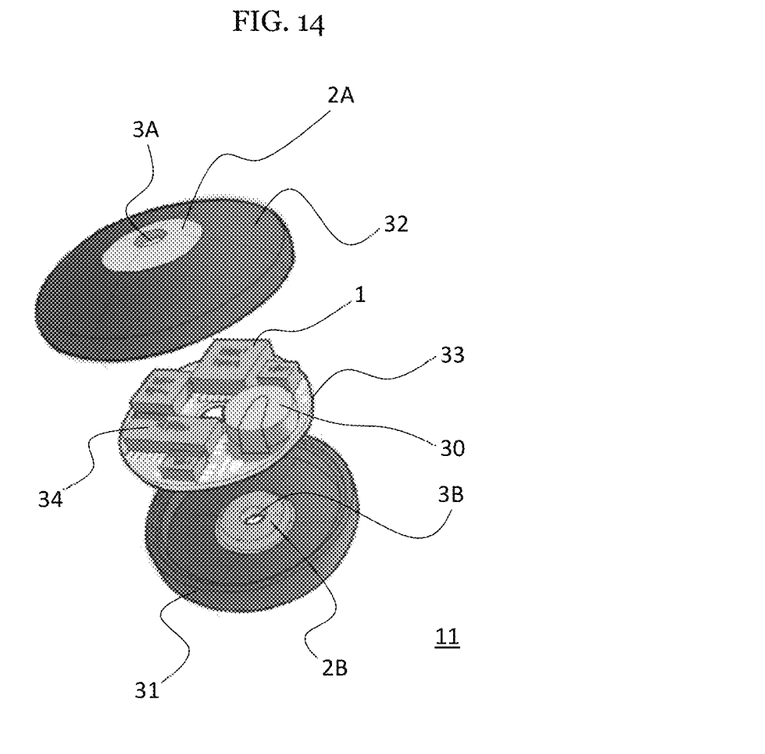
FIG. 14 is a exploded view of an exemplary medical guidance device.

FIG. 14 shows the exemplary medical guidance device 11 with mechanical interfaces 2A and 2B and tool guide 3A and 3B in this embodiment. FIG. 15 is an exploded view of the medical guidance device 11. In this embodiment, the medical guidance device 11 is one-patient use device and disposable after the treatment. The angular sensor 1 is housed by base housing 31 and top housing 33, and is powered by battery 30. The battery 30 also powers the wireless communication module 34 as well as all electronics in the circuit board 33. The base and top housing 31, 33 have mechanical interfaces 2A and 2B. The mechanical interfaces 2A and 2B includes through holes as tool guides 3A and 3B. These tool guides 3A and 3B are concentric each other and shares the same axis, which is defined as one of the default axis of the coordinate system in the angular sensor 1. The circuit board 33 also has a through hole that creates a channel from the tool guide 3A to the toll guide 3B. This channel is mated with the insertable medical tool 7.

Figure 15:
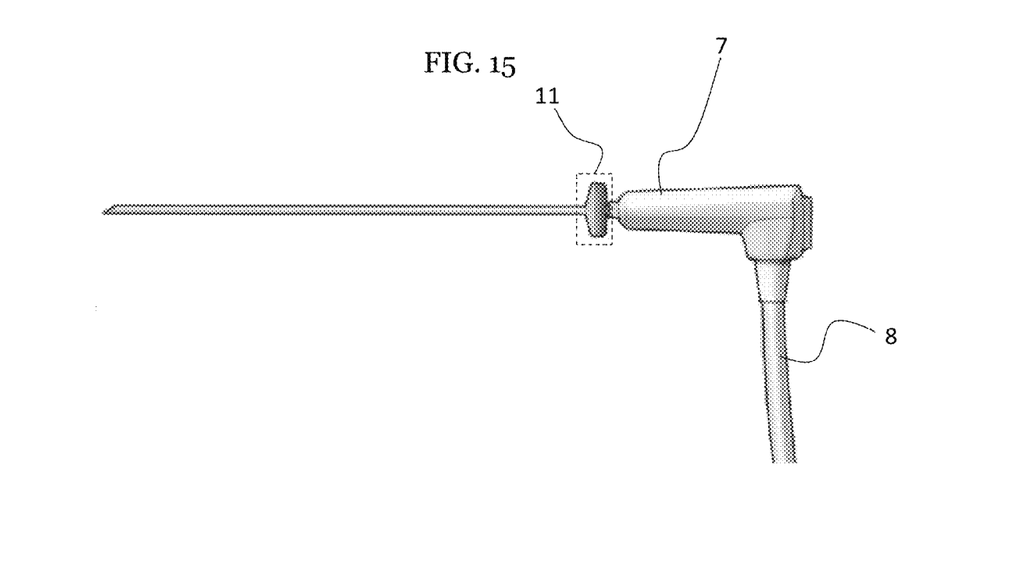
FIG. 15 shows the exemplary medical guidance device of FIG. 14 positioned on a needle insertion device.

FIG. 15 is a side view of the assembly of the exemplary medical guidance device 11 and the insertable medical tool 7. The insertable medical tool 7 in this embodiment is an ablation probe to ablate soft tissues. The medical guidance device 11 is attached to proximal end of the needle-like probe part in the insertable medical tool 7. Practitioners can attach the medical guidance device 11 to the tool guide 3A and 3B before the insertable medical tool 7 is used for treatments. The tool guide 3A and 3B contact the needle-like probe part and align the orientation of the needle-like probe to the axis of the tool guide 3A and 3B. The tool guide 3A and 3B have appropriate mechanical compliance and friction to the needle-like probe and can hold the medical guidance device 11 at the desired position in the needle-like probe.

The tool guide 3A and 3B can be configured and designed to have the appropriate diameter to fit around the gauge (diameter) of a needle-like probe part. By attaching the tool guide 3A and 3B to the needle-like probe part, the medical guidance device 11 can fit a variety of different insertable medical tool 7 with the same gauge of the needle-like probe part. Therefore, the medical guidance device 11 can be compatible to sweeping range of the insertable medical tool 7 with the needle-like probe part. Moreover, the tool guide 3A and 3B also can incorporate a gauge tube to fit a different gauge of the needle-like probe. Consequently, the tool guide 3A and 3B can fit the different gauges with the same tool guide 3A and 3B. Also, the gauge tube can seal inside of the medical guidance device 11 from the environment and can avoid malfunction and contamination.

(Application)

In use, the medical guidance device provides a real-time orientation of the insertable medical tools or the practitioner's hands directly. Therefore, the device can reduce or eliminate an orientation error when the insertable medical tools or the practitioner's hands are moving or dislocate from initial orientation. Also, the device can provide flexibility of orientation of the insertable medical tools to the target orientation through any trajectories at any location. Moreover, the practitioner can continuously adjust the orientation during operation by using the real-time orientation, for example the practitioner can adjust the orientation of the needle-like device during the insertion.

This device, when used with vibration, can also allow the practitioner to determine a location or maintain a location through the use of vibration instead of visual cues, thus allowing the practitioner potentially use the medical guidance device while looking in a different direction.

Moreover, the medical guidance device enables to guide variety of the insertable medical tools including the existing medical tools by attaching the mechanical interface to the insertable medical tools or the practitioner's hands. Therefore, in conjunction with real-time orientation detection, the practitioner can perform the existing workflow to orient the insertable medical tools with minimal changes of the workflow. Also, by detaching the medical guidance device from the insertable medical tools or the practitioner's hands, the practitioner can easily and quickly change configuration of the insertable medical tools, which are types or individuals of the insertable medical tools for guidance, number of the medical guidance devices, places where the medical guidance devices attach and venue for the workflow, and can perform the desired workflow.

Also, by using inertial measurement unit, the device doesn't need to include a component that externally observes the orientation of the medical device to determine the orientation in three dimensional space. Therefore, the device can be miniaturized and can avoid to obstacle line of flow and line of sight of physician or other practitioners. Also, the device can be used in confined space, for example in inside of the bore of the medical imaging device or in space among the other medical devices in the operational room.

In some applications, an additional reference device is removably attached to a reference sensor. The reference device may be, for example, attached to a patient or inserted at a target point (i.e., a needle inserted into the lesion to be treated). Then, the discrepancy between the reference sensor on the reference device and the other angular sensors on the insertable medical tool to be guided and then inserted to the target point can guide the insertable medical tools from any reference that the practitioner is interested in. Exemplary, dynamic objects such as a patient's chest that moves with each breadth can be analyzed using the reference. The guidance device, the sensor, which, in this exemplary embodiment and others, may be an ultrasound probe and the patient surface during breathing, can be the reference. Therefore, the practitioners can plan and execute the guidance of the insertable medical tools taking account into dynamic motions in the guidance.

In some applications, a reference sensor attached on or near the patient can take into account the patient movement, for example turning over in the bed, breathing, heart beating, for the guidance of the insertable medical tools. A reference sensor that is located on an ultra sound imaging probe can register the orientation of the medical guidance device to the coordinate of the ultra sound images and enable to guide the insertable medical tools with real-time orientation associated with real-time ultra sound images.

By registering position of the skin entry point to the coordinate of the medical images, the system can also define a point where the trajectory of the medical device goes. With the orientation from the medical guidance device, the console can give feedback of the potential trajectory of the insertable medical tools associated with the medical image. Therefore, the practitioner can evaluate the trajectory with anatomical data.

In some embodiments the device is particularly useful during the insertion of multiple needles, such as during ablation therapy. Often, the positioning of a second and any subsequent needle placed in a patient is defined by the practitioner by the prior placement of the first needle. Thus, in use, the mechanical interface can be aligned with the first needle after its placement, such as by, for example, holding down a button (e.g., button 9 as shown in FIG. 3) for around 1 second while the mechanical interface is in substantially the same position as the first placed needle. Then, the second and any optional additional needles can be placed based on the relative position information of the first needle. In other embodiments, an indicator can be positioned on the first placed needle to indicate the orientation of the second or subsequent needle relative to the position information of the first needle. In some embodiments, the first needle may be placed by the methods as described herein, and in other embodiments, the first needle may be placed by using a needle positioning apparatus.

The devices and methods as disclosed herein may also be used in combination with a needle positioning apparatus, such as the apparatus disclosed in U.S. Pat. Pub. 2014/0275979, herein incorporated by reference in its entirety.

Software Related Disclosure

Embodiment(s) of the present invention comprising one or more of the circuit board, the console 13, the image server 15, and optionally the indicator 14 can also be realized by one or more computers that reads out and executes computer executable instructions (e.g., one or more programs) recorded on a storage medium to perform the functions of one or more of the above-described embodiment(s) and/or that includes one or more circuits for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

The details of an exemplary computer unit CU are described. A Computer system includes CPU, Storage/RAM, I/O Interface and user interface. Also, Computer system may comprises one or more devices. For example, the one computer may include the CPU, Storage/RAM, I/O Interface and other computers may include one or more user interfaces. The CPU is configured to read and perform computer-executable instructions stored in the Storage/RAM. The computer-executable instructions may include those for the performance of the methods and/or calculations described herein. For example, CPU calculates the center of the dark ring. Or, CPU calculates various values according to the information from the angular sensor, from the image server, from the signal interface. And so on. Storage/RAM includes one or more computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc.

Storage/RAM may store computer-readable data and/or computer-executable instructions. Each of components in the computer system communicates with each other via a bus. For example, the image date from, for example, a CT or MRI image is stored or sent through the image server 15 and may be stored in the storage/RAM. The image may then be displayed on a monitor with or without additional information from the medical guidance device 11 or user input such as a target orientation or discrepancy from the target orientation.

The I/O interface provides communication interfaces to input and output devices, which, in addition to the circuit board, indicator 14, the signal interface 12, and the image server 15, may include a communication cable, a network (either wired or wireless), or other devices. The I/O interface may be coupled to a user interface unit such as one or more of a keyboard, a mouse, a touch screen, a light pen, a microphone and so on.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The term "attached" includes both direct and indirect attachment (e.g., with an intermediary component). All attachments may be removable attachments such that a user may attach and detach multiple times, depending on need. The attachment should be sufficient such that, for example, the medical device does not separate from the mechanical interface. The attachment may be designed for single handed attachment and/or detachment.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

The invention claimed is:

1. A medical guidance device configured to guide an insertable medical tool for insertion into a patient through a skin entry point comprising:
    an angular sensor comprising:
        an inertial measurement unit comprising at least one sensor that is a gyroscope,
        an accelerometer or a magnetometer, and
        a circuit board connected to the inertial measurement unit and configured to compute an orientation by processing sensed signals from the inertial measurement unit;
    a mechanical interface attached to the angular sensor; and
    an indicator configured to be mounted on the patient and at least partially surrounds the skin entry point, the indicator is configured to
        (i) receive information about the orientation from the angular sensor and
        (ii) provide real-time feedback to a practitioner by indicating the orientation for the insertable medical tool,
    wherein the mechanical interface is configured to be removably attached to the insertable medical tool or the practitioner.

2. The medical guidance device according to claim 1, wherein the inertial measurement unit comprises the gyroscope, the accelerometer and the magnetometer, and the circuit board is configured to compute the orientation by processing sensed signals from the gyroscope, the accelerometer and the magnetometer.

3. The medical guidance device according to claim 1 further comprising;
    a signal interface connected to the circuit board, wherein the signal interface is configured to receive a target orientation signal, and the circuit board is configured to compute a discrepancy between the target orientation and the orientation determined by the inertial measurement unit.

4. The medical guidance device according to claim 1 further comprising;
    a data storage unit connected to the circuit board;
    wherein the data storage stores the orientation determined by the inertial measurement unit.

5. The medical guidance device according to claim 4 further comprising;
    a user interface that is configured to trigger the circuit board based on the practitioner's operation,
    wherein the circuit board is configured to:
        set the orientation in the event of the trigger from the user interface as a reference orientation,
        command the data storage unit to store the reference orientation, and
        compute discrepancy between the reference orientation in the data storage and the orientation determined by the inertial measurement unit.

6. The medical guidance device according to claim 5 wherein the reference orientation is the orientation between the insertable medical tool and a second insertable medical tool, and the circuit board is configured to compute discrepancy between different insertable medical tools.

7. The medical guidance device according to claim 5 further comprising;
    one or more reference markers to define geometrical relation with a coordinate of the inertial measurement unit;
    wherein the one or more reference markers is aligned to an image scan direction of a medical imaging device, the circuit board is configured to set the reference orientation based on the one or more aligned reference markers.

8. The medical guidance device according to claim 7, wherein a gravitational orientation detected in the inertial measurement unit is aligned to the gravitational orientation in the image.

9. The medical guidance device according to claim 1, wherein information provided by the indicator is real-time feedback of the orientation.

10. The medical guidance device according to claim 1, wherein the medical guidance device is configured to guide a needle-like device.

11. The medical guidance device according to claim 1, wherein the indicator is mounted on the mechanical interface.

12. The medical guidance device according to claim 1, further comprising;
a second mechanical interface mechanically connected to the indicator
wherein the indicator is configured to be removably attachable to a location selected by the practitioner.

13. A medical guidance system comprising;
a plurality of the medical guidance devices according to claim 1;
a processor electrically connected to the plurality of medical guidance devices;
wherein the processor sets one of the plurality of medical guidance devices as a reference device, and
the processor measures discrepancies between an orientation of the reference device and orientations of the other medical guidance devices.

14. The medical guidance system according to claim 13, wherein the reference device is configured to attach onto the patient, and at least one medical guidance device from the plurality of medical guidance devices is attached on a needle-like device configured to be inserted into the patient body.

15. The medical guidance system according to claim 13, wherein the reference device is the medical guidance device attached on an ultrasound imaging probe, and at least one of the other medical guidance devices is attached on a needle-like device to be inserted into the patient body.

16. A medical guidance system comprising;
at least one medical guidance device according to claim 1 attached on a needle-like device;
fiducial markers on a patient to be aligned to a skin entry point where the needle-like device is inserted
a console electrically connected to an image server and the medical guidance device;
wherein the console receives a medical image, and registers a position and the orientation of the fiducial markers to a coordinate system of the patient, and feedback the orientation from the medical guidance device on the medical image by using the skin entry point as a reference position.

17. A method of deploying an insertable medical tool into a patient comprising:
attaching a mechanical interface to an insertable medical tool, wherein the mechanical interface is part of a medical guidance device that comprises:
an angular sensor comprising an inertial measurement unit comprising at least one sensor that is a gyroscope, an accelerometer or a magnetometer, and a circuit board connected to the inertial measurement unit,
a mechanical interface attached to the angular sensor, and
an indicator configured to be mounted on the patient that receives information about the orientation from the angular sensor and provide real-time feedback to a practitioner by indicating the orientation of the insertable medical tool;
defining a reference orientation,
aligning the insertable medical tool with the reference orientation based on the feedback from the indicator, and
deploying the insertable medical tool into the patient.

18. A method of aiding in a deployment of an insertable medical tool comprising:
providing the insertable medical tool comprising:
an angular sensor comprising an inertial measurement unit comprising at least one sensor that is a gyroscope, an accelerometer or a magnetometer, and a circuit board connected to the inertial measurement unit, and
a mechanical interface attached to the angular sensor, and configured for attachment to the insertable medical tool, and
an indicator configured to be mounted on a patient or a patient's bed that receives information about an orientation of the insertable medical tool from the angular sensor and provide real-time feedback to a practitioner by indicating the orientation of the insertable medical tool;
accepting a reference orientation information via a user input;
evaluating discrepancy between the insertable medical tool orientation and/or location compared to the reference orientation; and
providing discrepancy information via the indicator.

19. The method of claim 18, wherein the angular sensor comprise each of the gyroscope, the accelerometer and the magnetometer.

20. A system comprising:
a medical guidance device comprising:
an angular sensor comprising:
an inertial measurement unit comprising at least one sensor that is a gyroscope, an accelerometer or a magnetometer, and
a circuit board connected to the inertial measurement unit and configured to compute an orientation by processing sensed signals from the inertial measurement unit;
a mechanical interface attached to the angular sensor;
wherein the mechanical interface is configured to be removably attached to an insertable medical tool or a practitioner, and
wherein the angular sensor is configured to determine an orientation of the insertable medical tool, and
an indicator configured to be mounted on a patient or a patient's bed that receives information about the orientation from the angular sensor and provide real-time feedback to the practitioner by indicating the orientation of the insertable medical tool.

21. The medical guidance device of claim 1, wherein indicating the orientation for the insertable medical tool comprises indicating information of insertion plane direction $\Phi$ and insertion angle $\theta$.

22. The system of claim 20, wherein indicating the orientation for the insertable medical tool comprises indicating information of insertion plane direction $\Phi$ and insertion angle $\theta$.

* * * * *